US00PP19210P2

(12) United States Plant Patent
van Gaalen

(10) Patent No.: US PP19,210 P2
(45) Date of Patent: Sep. 9, 2008

(54) *PHLOX* PLANT NAMED 'PURE FEELINGS'

(50) Latin Name: *Phlox paniculata*
Varietal Denomination: Pure Feelings

(76) Inventor: René van Gaalen, Sionsweg 26, 2286 KL Rijswijk (NL)

( * ) Notice: Subject to any disclaimer, the term of this patent is extended or adjusted under 35 U.S.C. 154(b) by 0 days.

(21) Appl. No.: 11/800,793

(22) Filed: May 7, 2007

(51) Int. Cl.
*A01H 5/00* (2006.01)

(52) U.S. Cl. ..... Plt./320

(58) Field of Classification Search ..... Plt./320
See application file for complete search history.

*Primary Examiner*—Kent L. Bell
*Assistant Examiner*—S. B. McCormick-Ewoldt
(74) *Attorney, Agent, or Firm*—C. A. Whealy

(57) ABSTRACT

A new and distinct cultivar of *Phlox* plant named 'Pure Feelings', characterized by its upright plant habit; freely flowering habit; double green and white bi-colored flowers; sterile flowers; and good postproduction longevity.

2 Drawing Sheets

Botanical designation: *Phlox paniculata.*
Cultivar denomination: 'Pure Feelings'.

BACKGROUND OF THE INVENTION

The present invention relates to a new and distinct cultivar of *Phlox,* botanically known as *Phlox paniculata* and hereinafter referred to by the name 'Pure Feelings'.

The new *Phlox* is a naturally-occurring whole plant mutation of the *Phlox paniculata* cultivar Natural Feelings, disclosed in U.S. Plant Pat. No. 13,623. The new *Phlox* was discovered and selected by the Inventor as a single flowering plant within a population of plants of 'Natural Feelings' in a controlled environment in Noordwijkerhout, The Netherlands in July, 2003.

Asexual reproduction of the new *Phlox* by cuttings in a controlled environment in Rijswijk, The Netherlands since January, 2006, has shown that the unique features of this new *Phlox* are stable and reproduced true to type in successive generations.

SUMMARY OF THE INVENTION

The cultivar Pure Feelings has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Pure Feelings'. These characteristics in combination distinguish 'Pure Feelings' as a new and distinct cultivar of *Phlox:*

1. Upright plant habit.
2. Freely flowering habit.
3. Double green and white bi-colored flowers.
4. Sterile flowers.
5. Good postproduction longevity.

Plants of the new *Phlox* differ from plants of the parent, the cultivar Natural Feelings, primarily in flower color as plants of the cultivar Natural Feelings have pink and green bi-colored flowers.

Plants of the new *Phlox* can be compared to plants of the cultivar Popeye, not patented. In side-by-side comparisons conducted in Den Hoorn, The Netherlands, plants of the new *Phlox* and the cultivar Popeye differed in the following characteristics:

1. Plants of the new *Phlox* were more freely flowering than plants of the cultivar Popeye.
2. Plants of the new *Phlox* had white and green bi-colored flowers whereas plants of the cultivar Popeye had pale pink-colored flowers.
3. Flowers of plants of the new *Phlox* were sterile whereas flowers of plants of the cultivar Popeye were fertile.

BRIEF DESCRIPTION OF THE PHOTOGRAPHS

The accompanying colored photographs illustrate the overall appearance of the new *Phlox,* showing the colors as true as it is reasonably possible to obtain in colored reproductions of this type. Colors in the photographs may differ slightly from the color values cited in the detailed botanical description which accurately describe the colors of the new *Phlox.*

The photograph on the first sheet comprises a side perspective view of a typical flowering plant of 'Pure Feelings' grown in an outdoor nursery.

The photograph on the second sheet is a close-up view of a typical inflorescence of 'Pure Feelings'.

DETAILED BOTANICAL DESCRIPTION

The aforementioned photographs and following observations, measurements and values describe plants grown in Den Hoorn, The Netherlands, under commercial practice during the summer in an outdoor nursery with day temperatures ranging from 15° C. to 35° C. and night temperatures ranging from 10° C. to 18° C. Plants were grown for about one year when the photographs and description were taken. In the following description, color references are made to The Royal Horticultural Society Colour Chart, 2001 Edition, except where general terms of ordinary dictionary significance are used.

Botanical classification: *Phlox paniculata* cultivar Pure Feelings.

Parentage: Naturally-occurring whole plant mutation of the *Phlox paniculata* cultivar Natural Feelings, disclosed in U.S. Plant Pat. No. 16,623.

Propagation:

*Type.*—By cuttings.

*Time to produce a rooted plant.*—About three weeks at 20° C.

*Root description.*—Medium thickness; white in color.

*Rooting habit.*—Freely branching; dense.

Plant description:

*Plant form/habit.*—Upright plant habit; roughly conical in shape; moderately vigorous growth habit. Moderately freely basal branching habit.

*Plant height.*—About 78 cm.

*Plant width* (*spread*).—About 48 cm.

*Stem length* (*excluding inflorescence*).—About 59.2 cm.

*Stem diameter.*—About 5 mm.

*Internode length.*—About 3.6 cm.

*Stem strength.*—Strong.

*Stem texture.*—Smooth, glabrous.

*Stem color.*—143B.

Foliage description:

*Arrangement.*—Opposite, simple.

*Length.*—About 11.3 cm.

*Width.*—About 2.9 cm.

*Shape.*—Elliptic to narrowly elliptic.

*Apex.*—Acute.

*Base.*—Attenuate.

*Margin.*—Entire.

*Texture, upper and lower surfaces.*—Smooth, glabrous.

*Venation pattern.*—Pinnate. Color: Developing leaves, upper surface: 137B to 137C. Developing leaves, lower surface: 137B. Fully expanded leaves, upper surface: 137A; venation, 143C to 144A. Fully expanded leaves, lower surface: 137C; venation, 143C to 144A. Petiole: Length: About 1.5 mm. Diameter: About 4 mm. Texture, upper and lower surfaces: Smooth, glabrous. Color, upper and lower surfaces: 143C.

Flower description:

*Flower type/habit.*—Double salverform flowers arranged in terminal panicles; flowers face upright and outward. Panicles roughly hemispherical in shape. Freely flowering habit with about 750 flower buds and flowers developing per flowering stem.

*Fragrance.*—None detected.

*Natural flowering season.*—Continuously flowering from June through August in The Netherlands. Flowers not persistent.

*Postproduction longevity.*—Flowers last about 10 to 14 days on the plant and about 10 days as a cut flower.

*Flower buds.*—Height: About 7 mm. Diameter: About 2.5 mm. Shape: Oblong. Color: 145B to 145C.

*Inflorescence height.*—About 18.8 cm.

*Inflorescence diameter.*—About 17.6 cm.

*Flower diameter.*—About 1.9 cm.

*Flower depth.*—About 1.9 cm.

*Petals.*—Quantity per flower: Typically five in a single whorl; petals fused at the base into a narrow tube. Length: About 1.9 cm. Lobe width: About 5 mm. Shape, lobe: Spatulate. Apex: Cuspidate. Margin: Entire. Texture, upper and lower surfaces: Smooth, glabrous. Color: Developing and fully expanded petals, upper surface: 143B to 144C; towards the margin, close to 155D; throat, 186B to 186C. Developing and fully expanded petals, lower surface: N186D; towards the apex, 146B; at the margin, between 145C to 145D and close to 155D; tube, N186D.

*Petaloids.*—Quantity per flower: Typically five in a single whorl; petals fused at the base into a narrow tube. Length: About 9 mm. Lobe width: About 2 mm. Shape: Oblanceolate. Apex: Cuspidate. Margin: Entire. Texture, upper and lower surfaces: Smooth, glabrous. Color: Immature, upper and lower surfaces: 144B. Mature, upper and lower surfaces: 144B to 144C.

*Sepals.*—Quantity per flower: Typically five in a single whorl, fused towards the base; campanulate calyx. Length: About 9 mm. Width: About 1 mm. Shape: Lanceolate. Apex: Narrowly apiculate. Margin: Entire. Texture, upper and lower surfaces: Smooth, glabrous. Color, developing sepals, upper and lower surfaces: 146A. Color, fully expanded sepals, upper and lower surfaces: N187A tinged with 147A.

*Peduncles.*—Length: About 16 cm. Diameter: About 3 mm. Angle: Main peduncle, erect; lateral peduncles, about 40° to 50° From vertical. Strength: Strong. Texture: Smooth, glabrous. Color: 143A.

*Pedicels.*—Length: About 4 mm. Diameter: About 1 mm. Angle: Erect to about 60° from vertical. Strength: Strong. Texture: Smooth, glabrous. Color: 143A to 143B.

*Reproductive organs.*—Development of reproductive organs has not been observed.

*Seed/fruit.*—Seed and fruit development have not been observed.

Disease/pest resistance: Plants of the new *Phlox* have not been noted to be resistant to pathogens and pests common to *Phlox*.

Garden performance: Plants of the new *Phlox* have been observed to have good garden performance and tolerance rain, wind and temperatures ranging from about 0° C. to about 30° C.

It is claimed:

1. A new and distinct *Phlox* plant named 'Pure Feelings' as illustrated and described.

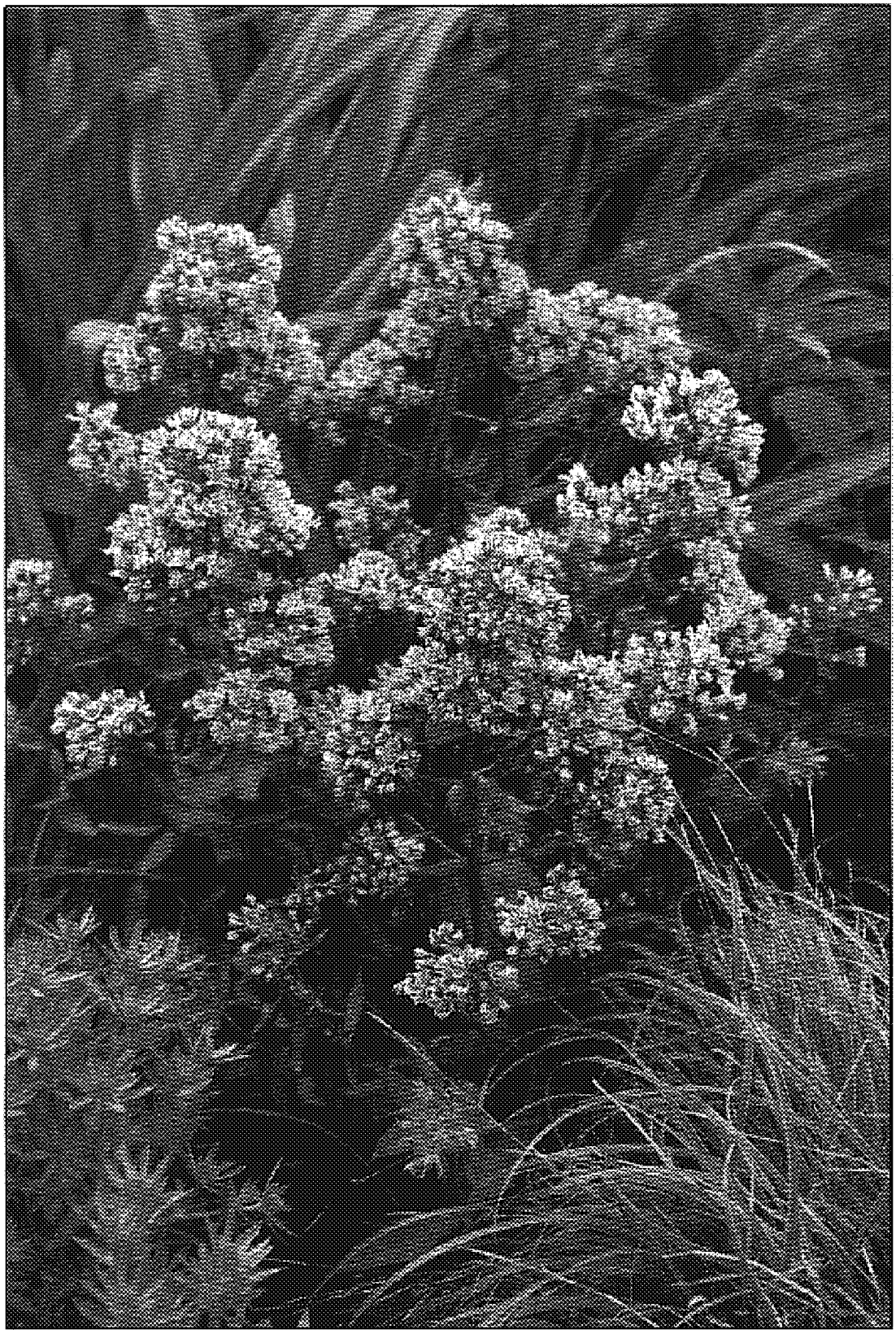

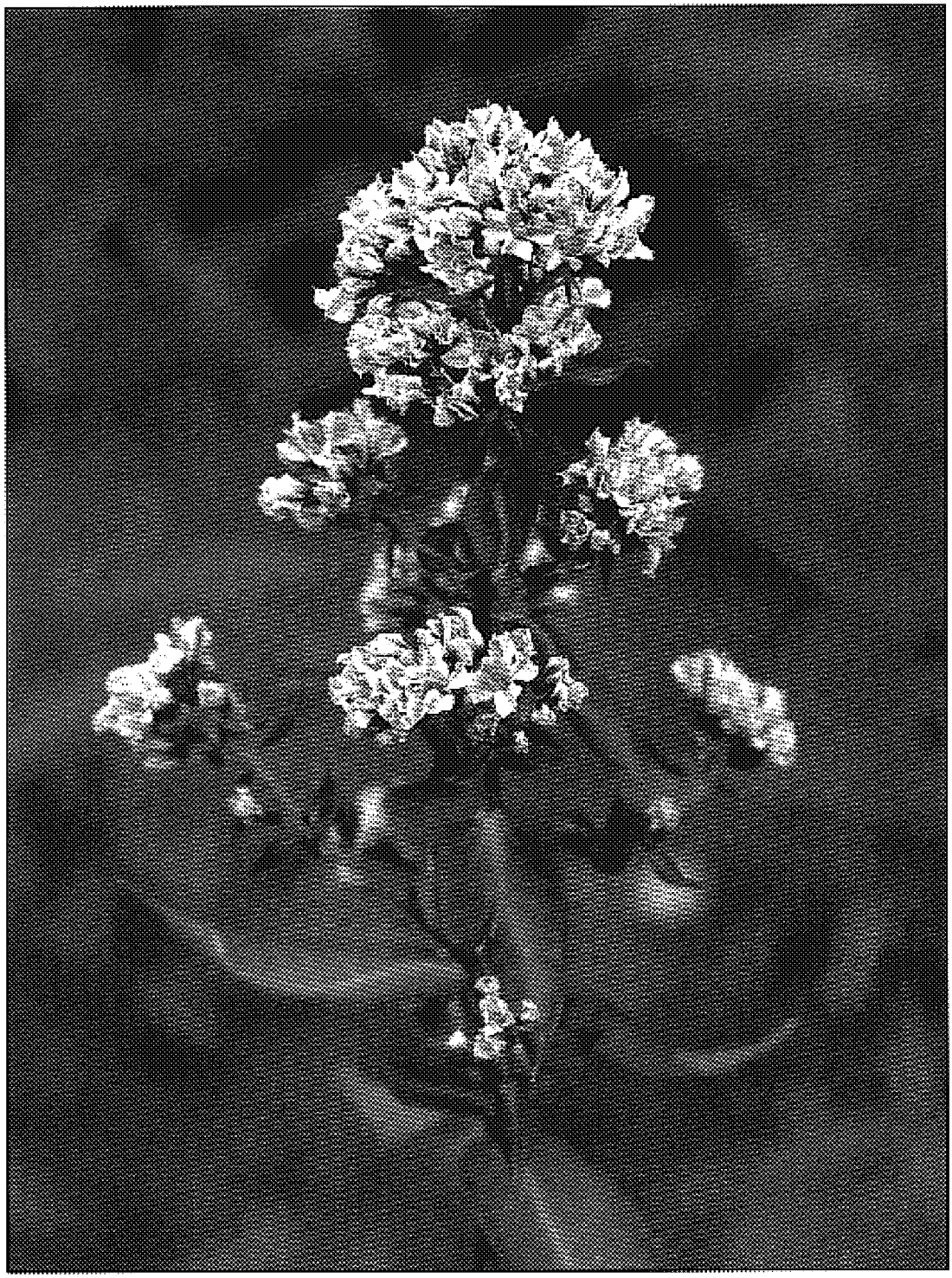

* * * * *